United States Patent
Stark

(10) Patent No.: US 8,029,658 B2
(45) Date of Patent: Oct. 4, 2011

(54) DEVICE AND METHOD FOR FILTRATION AND/OR SEPARATION OF MOLECULES, PARTICULARLY PROTEINS

(75) Inventor: Peter Stark, Schoenenbuch (CH)

(73) Assignee: Portmann Instruments A.G., Biel-Benken (CH)

( * ) Notice: Subject to any disclaimer, the term of this patent is extended or adjusted under 35 U.S.C. 154(b) by 1144 days.

(21) Appl. No.: 10/592,581

(22) PCT Filed: Mar. 18, 2005

(86) PCT No.: PCT/IB2005/000695
§ 371 (c)(1),
(2), (4) Date: Sep. 13, 2006

(87) PCT Pub. No.: WO2005/090962
PCT Pub. Date: Sep. 29, 2005

(65) Prior Publication Data
US 2007/0191596 A1 Aug. 16, 2007

(30) Foreign Application Priority Data
Mar. 18, 2004 (FR) ..................... 04 02781

(51) Int. Cl.
*G01N 27/26* (2006.01)
(52) U.S. Cl. ..................... 204/644
(58) Field of Classification Search .......... 204/644
See application file for complete search history.

(56) References Cited

U.S. PATENT DOCUMENTS

| 6,071,395 A | 6/2000 | Lange |
| 6,537,434 B1 | 3/2003 | McGrath et al. |
| 6,660,149 B1 | 12/2003 | Karger et al. |
| 6,685,811 B1 | 2/2004 | Laurin |

FOREIGN PATENT DOCUMENTS

| DE | 19948049 | | 12/2000 |
| DE | 10111853 | | 11/2002 |
| FR | 2760844 | | 9/1998 |
| WO | WO 9915875 | | 4/1999 |
| WO | WO 0136449 | | 5/2001 |
| WO | WO 0175432 | | 10/2001 |
| WO | WO 0186279 | | 11/2001 |
| WO | WO 02/054052 A1 | * | 7/2002 |
| WO | WO 03101591 | | 12/2003 |

* cited by examiner

*Primary Examiner* — Arun S Phasge
(74) *Attorney, Agent, or Firm* — Davis & Bujold, P.L.L.C.

(57) ABSTRACT

The present invention concerns a device and a method for filtering molecules that is precise, efficient, reliable, and rapid; it has a low rate of molecular loss, it can be upgraded, and it provides for the automated filtration of molecules according to one or more predefined parameters. The device (10) for filtration of molecules (3) comprises three filtration zones (11a-11c), each equipped with filtration reservoirs (1) in which a solution containing molecules (3) to be filtered is placed. The filtration reservoirs (1) are separated into two chambers by an isoelectric filter (4) which allows only selective passage of molecules (3) according to their isoelectric point (pI) when they are subjected to an electrical field generated by electrodes (5). This filtration device (10) comprises a mechanized tool holder (20) specifically for supporting one or more pairs of electrodes (5) in order to perform isoelectric filtration in one or more filtration reservoirs (1) simultaneously.

20 Claims, 6 Drawing Sheets

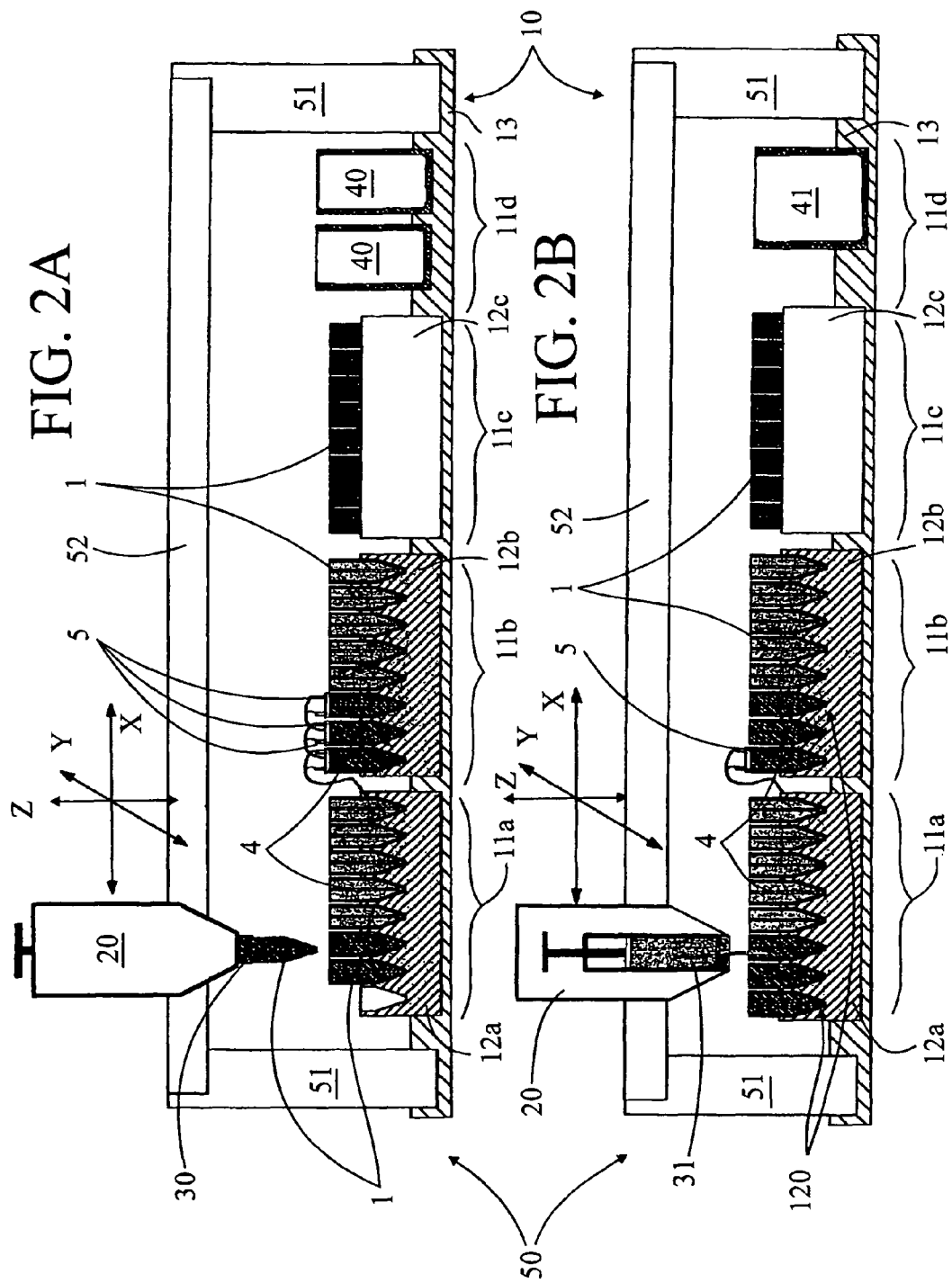

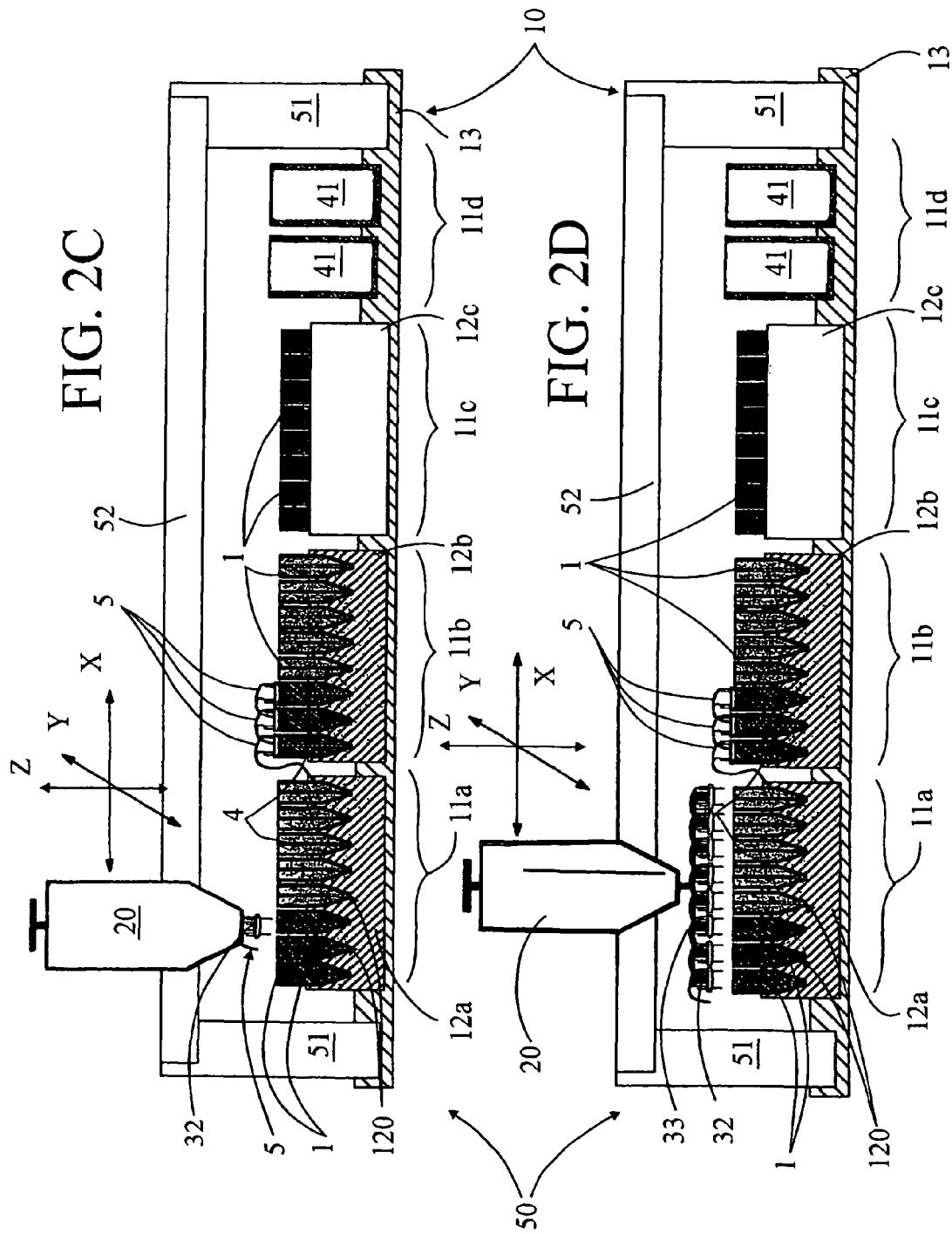

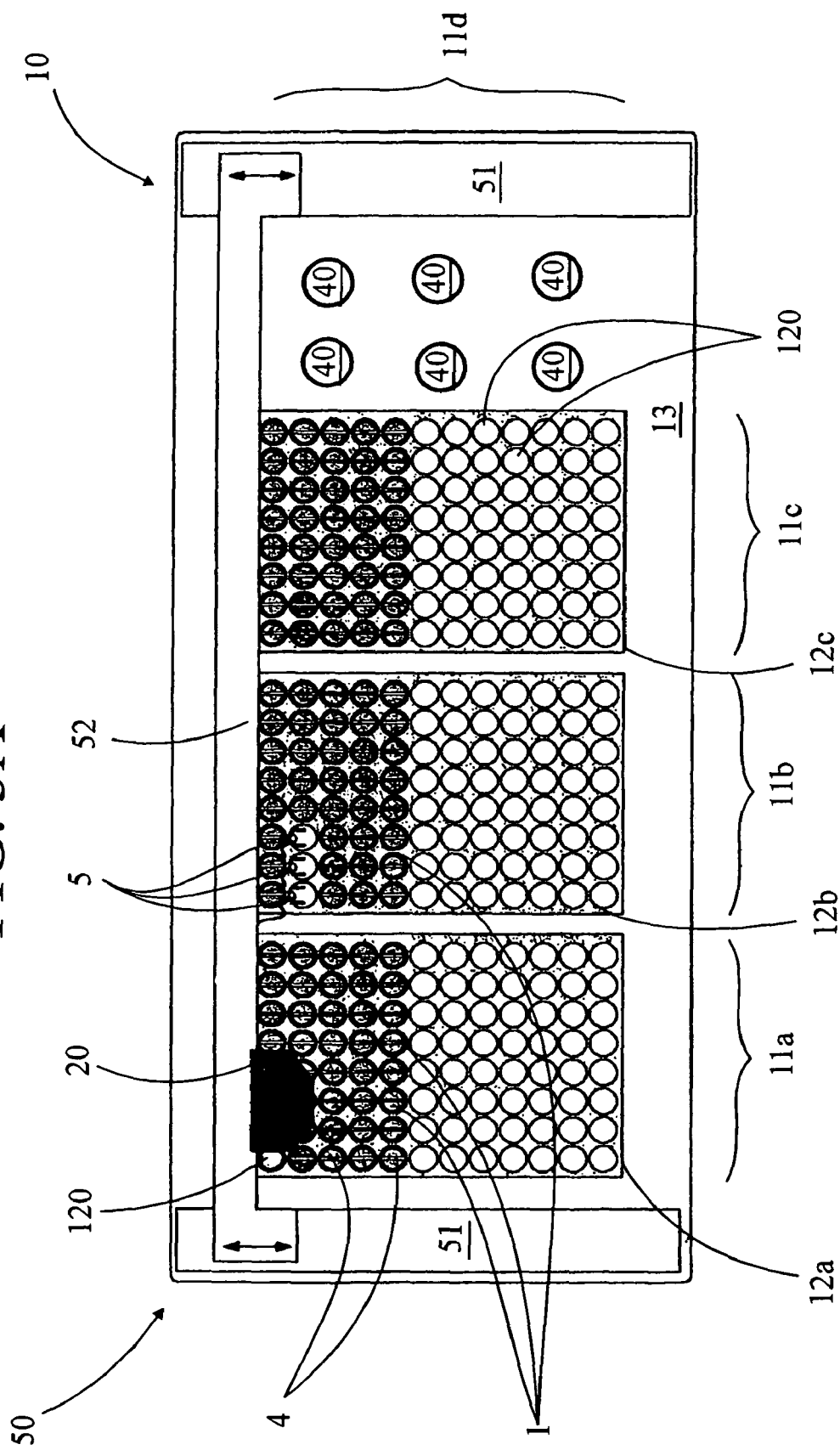

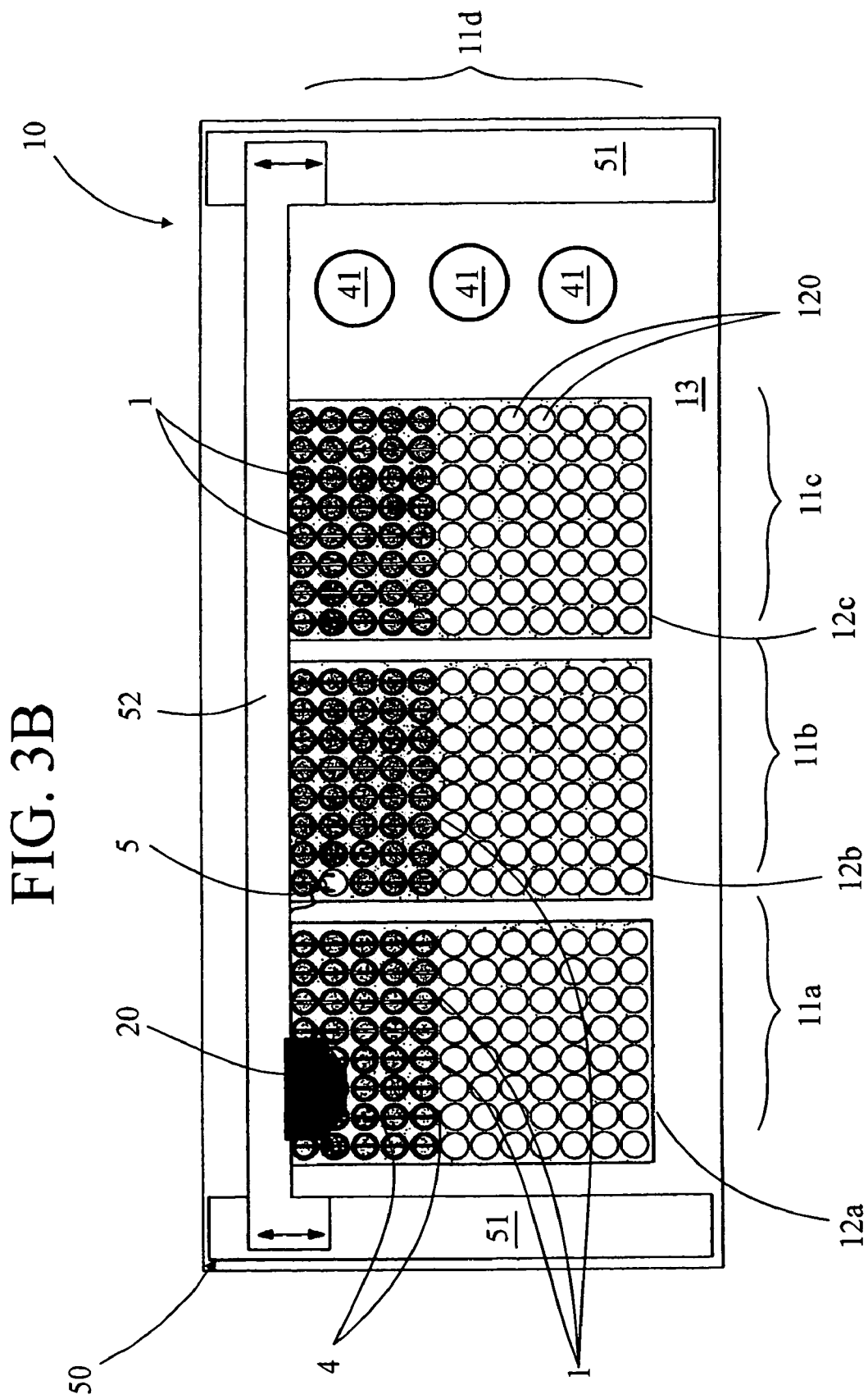

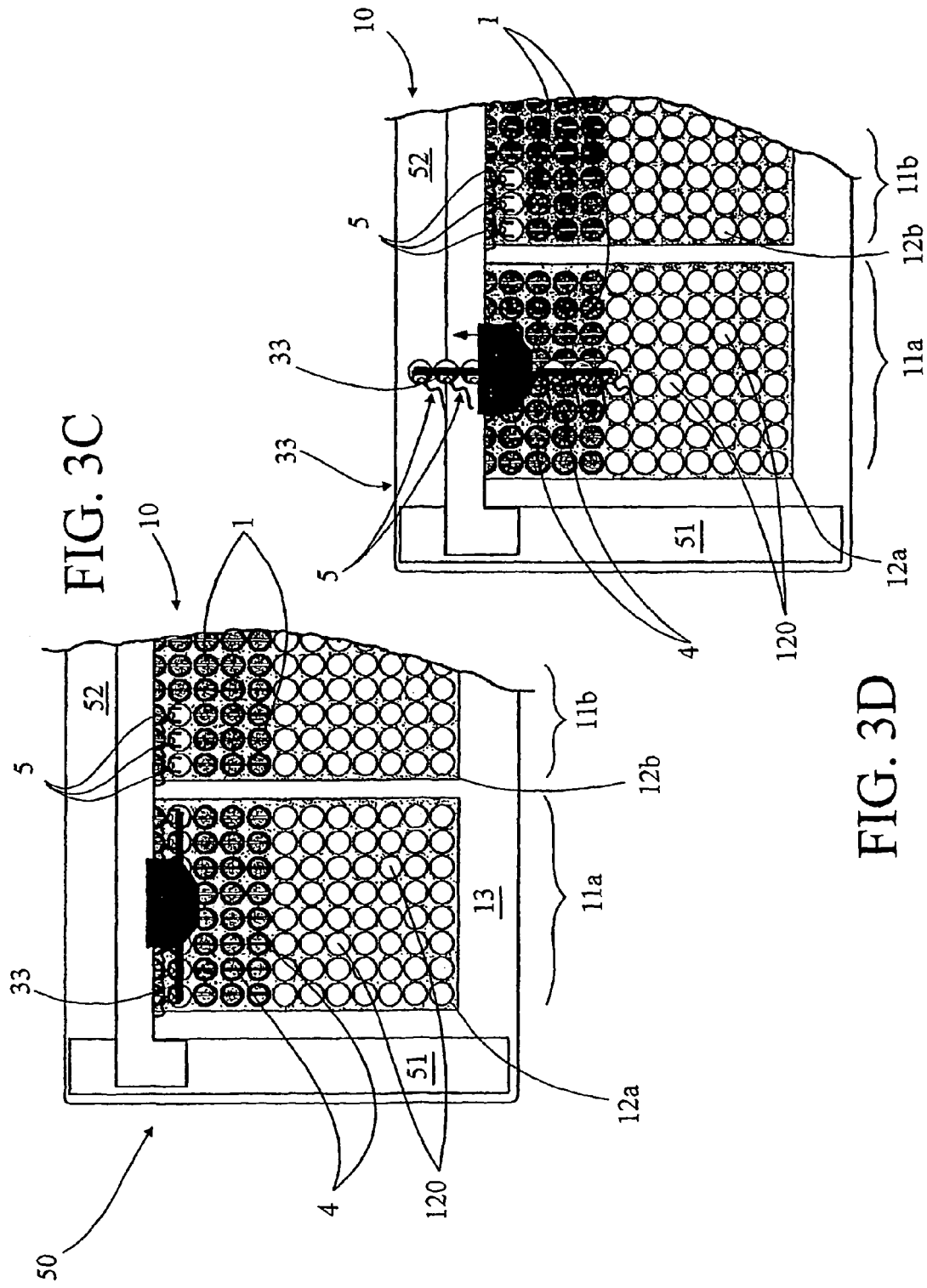

DEVICE AND METHOD FOR FILTRATION AND/OR SEPARATION OF MOLECULES, PARTICULARLY PROTEINS

This application is a national stage completion of PCT/IB2005/000695 filed Mar. 18, 2005 which claims priority from French Application Serial No. 04/02781 filed Mar. 18, 2004.

TECHNICAL DOMAIN

The present invention concerns a device for the filtration and/or separation of molecules, particularly proteins, equipped with at least one filtration zone comprising at least one filtration reservoir for receiving a solution containing the molecules to be filtered, said filtration reservoir being equipped with a filtration means separating it into at least two chambers for filtering the molecules according to at least one predetermined physical and/or chemical parameter, said filtration device also comprising the means for generating at least one electrical field which tends to cause displacement of the molecules from one chamber to the other through said filtration means. The invention also concerns a method for filtering and/or separating molecules implementing said device.

PRIOR ART

Several techniques are already known for separating and/or filtering molecules, such as, for example, electrophoresis (CE), isoelectric focalization (CIEF), electric or liquid chromatography (CEC and CLC).

The basic principle of isoelectric focalization (CIEF) consists of splitting molecules, such as proteins, according to their isoelectric point (pI), using chemical membranes such as those described in publication WO-A-01/86279.

Splitting molecules, an example of which is given in publication WO-A-01/75432, is achieved by performing the various steps described below.

In the first step, a filtration reservoir is prepared in which a pH gradient is created. To do this, a solution containing polyelectrolytes called ampholytes may be used, which carry a certain number of positively or negatively ionizing groups (amines, carboxyls or sulfates) and possess a certain buffering ability.

In the second step, the ampholytes in this solution are submitted to an electrical field, for example using two electrodes, an anode, and a cathode, located at the opposite extremities of the filtration reservoir. Under the influence of the electrical field, the ampholytes are displaced and positioned in the order of their own pI where they become immobilized. Their buffering capability helps the ampholytes to maintain a pH zone around them that is equal to their pI. A series of ampholytes having a pI covering a certain range of pH thus creates a continuous pH gradient. Consequently, the market offers a large number of ampholyte mixtures covering either very narrow or very broad pH ranges.

In a third step, the charged molecules, such as proteins, for example, are placed in this filtration reservoir and subjected to an electrical field generated by the electrodes in order to cause displacement of the molecules. The charged molecules migrate until they attain the pH corresponding to their pI, where their net charge is null, and become immobilized.

In a fourth step, the molecules arranged according to their pH are removed, using a pipette, for example.

In this way gradients of diverse pH amplitudes are created by combining several ampholytes. For example, it is possible to obtain fine gradients (e.g. 0.1 pH unit) over narrow pH ranges (e.g. between pH 5 to 7 or 6 to 8), particularly for achieving very fine separation and precisely measuring pI. Conversely, it is also possible to created a broad gradient (e.g. 0.4 pH unit) for a wider pH range (e.g. between pH 2 to 10), particularly for analyzing a large number of proteins.

Another filtration method partially based on the same principle is described in Publication WO-A-03/101591. This filtration method consists of using a first electrical current to separate the molecules according to their pH, then applying to molecules of a given pH a second electrical current allowing them to be separated according to another characteristic such as, for example, size.

Whatever the filtration method used, separation of molecules requires numerous operations that are sometimes repetitive, making it a lengthy, prohibitively expensive procedure. Furthermore, one of the major disadvantages of these molecular filtration methods resides in the fact that at the isoelectric point (pI), proteins, for example, are not very soluble and may precipitate. Therefore it is impossible to use them and the proportion lost may be considerable. Moreover, these filtration methods require excellent dexterity on the part of the user and specialized training, making them expensive to implement, with these costs recurring each time the molecules are filtered again.

Therefore, to eliminate these disadvantages, other molecule filtration methods using several adjacent, aligned sampling pipettes have been developed. Two of them are described in Publication Nos. U.S. Pat. No. 6,660,149 and WO-A-01/36449. These filtration methods allow work to occur simultaneously on several filtration reservoirs. However, these filtration methods remain laborious to use. They cannot be upgraded, they are limited as to modes of operation, and they lack flexibility. These filtration methods, like the other known filtration methods, are therefore unsatisfactory.

In addition, Publications DE-A-199 48 049, FR-A-2 760 844, and U.S. Pat. No. 6,071,395 describe devices adapted to filter according to size nucleic acid molecules (ADN) with the same electrical charge, but they are not adaptable to the isoelectric filtration of proteins with different electrical charges.

Publication U.S. Pat. No. 6,685,811 describes a method for the bidirectional separation of molecules in which the molecules in gel are submitted along a first direction to isoelectric filtration provoked by two electrodes disposed at the extremities of a filtration corridor separated into several successive chambers by several membranes, and along a second direction, to filtration by size. The distance to be traveled by the molecules in the filtration corridor and the distance separating the electrodes are such that the molecules are displaced very slowly, with filtration possibly lasting more than ten hours. Thus, the results of this method are mediocre.

Publications DE-A-101 11 853, U.S. Pat. No. 6,537,434 and WO-A-99/15875 describe robots for removing the molecules in solution with pipettes in order to treat them, for example, with filtration. These robots are simple manipulators and do not perform the filtration operation itself.

DESCRIPTION OF THE INVENTION

The aim of the present invention is to overcome these disadvantages by proposing a filtration device and method, specifically using isoelectric focalization, allowing molecules to be filtered and/or separated according to their isoelectric point, primarily proteins of different electrical charges, said device and method being automated, upgradeable, flexible, precise, effective, reliable, quickly accomplished, and incurring minimal molecular loss. Thus, the filtration and/or separation can be used in industry, utilizing one or more predefined or random parameters and predefined or random sequences that are easily cataloged, thereby improving and facilitating the tracking of the separation and/or filtration operations performed.

For this purpose the invention concerns a filtration device of the type indicated in the preamble, characterized in that the filtration zone comprises a plurality of independent filtration reservoirs held by at least one support, the filtration means comprising at least one isoelectric filter for separating the molecules according to their isoelectric point, and the filtration device comprises at least one mechanized tool holder with at least one tool, at least two electrodes of which form the means for generating the electrical field to perform at least one isoelectric filtration, said tool holder being coupled with a displacement means for displacing at least the tool relative to the filtration zone, particularly for placing the electrodes in at least one filtration reservoir before filtration and removing them after filtration, said tool holder also being coupled with a computerized control means to control its displacement and the operation of the tools it carries, particularly the supply of electricity to the electrodes for performing isoelectric filtration.

According to a first embodiment, the displacement means comprises at least one carriage containing the tool holder, said carriage being movable along a chassis in order to displace the tool relative to the filtration zone. For this purpose, the displacement means comprises, for example, two rails generally parallel to each other and designed to guide the carriage in generally parallel translation relative to the filtration zone.

The rails may be supported by upright elements integral with the chassis and located on either side of the filtration zone. The rails may also be integral with the chassis, with the carriage then defining an overhead support.

Advantageously, the carriage advantageously comprises a slide along which said tool holder moves in translation.

According to a second embodiment, the displacement means comprises at least one articulated arm holding the tool holder.

The filtration device comprises several carriages and/or articulated arms and/or tool holders designed to be removable and interchangeable.

The filtration device advantageously comprises at least one tool holder dedicated to isoelectric filtration and one tool holder dedicated to manipulating the filtration reservoirs.

Preferably the filtration device comprises a complementary tool holder selected from the group consisting of a claw, an electromagnetic grip, a syringe-holder, gripping fingers or arm, jaws, a syringe, a piston, a suction device, or a vacuum system.

The support holding said reservoirs advantageously may be coupled with a complementary displacement means regulated by the control means for displacing said support in translation and/or in rotation relative to the filtration zone and/or the tool holder.

Preferably, the filtration device comprises at least one preparation zone provided for pre- and/or post-filtration operations such as: storage of molecules, rinsing, dilution, disinfecting, introducing additive, waste, or the other operations.

The preparation zone may be equipped with at least one container selected from the group consisting of a molecule storage container, a buffer container, a waste container, a solvent container, a cleaning container, or a container for chemical and/or biological reactions.

The filtration reservoir is advantageously selected from the group comprising a test tube, a flask, or a measurement beaker; and the filtration means preferably comprises the isoelectric filter located essentially in the axis of symmetry of the filtration reservoir. It may also comprise at least one complementary filter selected from the group consisting of cut-off filters, electrophoretic filters, or any other suitable filter designed to separate molecules according to size, electrical charge, or any other criteria.

The computerized control means is advantageously regulated by at least one central processor run by at least one computer program and the displacement means comprises at least one of the actuators chosen from the group comprising a motor, a cylinder, a reduction gear motor, or an electromagnet.

The filtration device is coupled with air conditioning means for regulating at least the temperature of the filtration reservoirs, for example, at least one thermally regulated enclosure capable of receiving said filtration device.

The invention also concerns a method for the filtration and/or separation of molecules, particularly proteins, during which:

a plurality of filtration reservoirs containing molecules in solution is disposed in at least one filtration zone, each filtration reservoir being separated into at least two chambers by at least one isoelectric filter designed to separate the molecules according to their isoelectric point;

an electrical field is applied to provoke displacement of at least a portion of the molecules from one chamber to the other through said isoelectric filter; and the molecules are recovered after filtration;

at least one of these operations being performed automatically by a mechanized tool holder equipped with at least one tool, having at least two electrodes for creating the electrical field to effect at least one isoelectric filtration, said tool holder being coupled with a displacement means and said tool holder also being coupled with a computerized control means programmed to displace at least the electrodes relative to the filtration zone and supply them with electricity to effect the isoelectric filtration.

SUMMARY DESCRIPTION OF THE DRAWINGS

The present invention and its features will be more apparent from the following description of one embodiment with reference to the attached drawings provided by way of non-limiting example, wherein:

FIGS. 2A through 2D are cross-sections of the filtration device according to the invention in the respective steps of displacement of a filtration reservoir, introduction of an additive into a filtration reservoir, unitary electrode displacement, and simultaneous electrode displacement;

FIG. 3A is an overhead view of the filtration device according to FIG. 2A;

FIG. 3B is an overhead view of the filtration device according to FIG. 2B; and

FIGS. 3C and 3D are overhead views of the filtration device according to FIG. 2D, with the electrode support shown in two different positions.

Figures 1A, 1B:
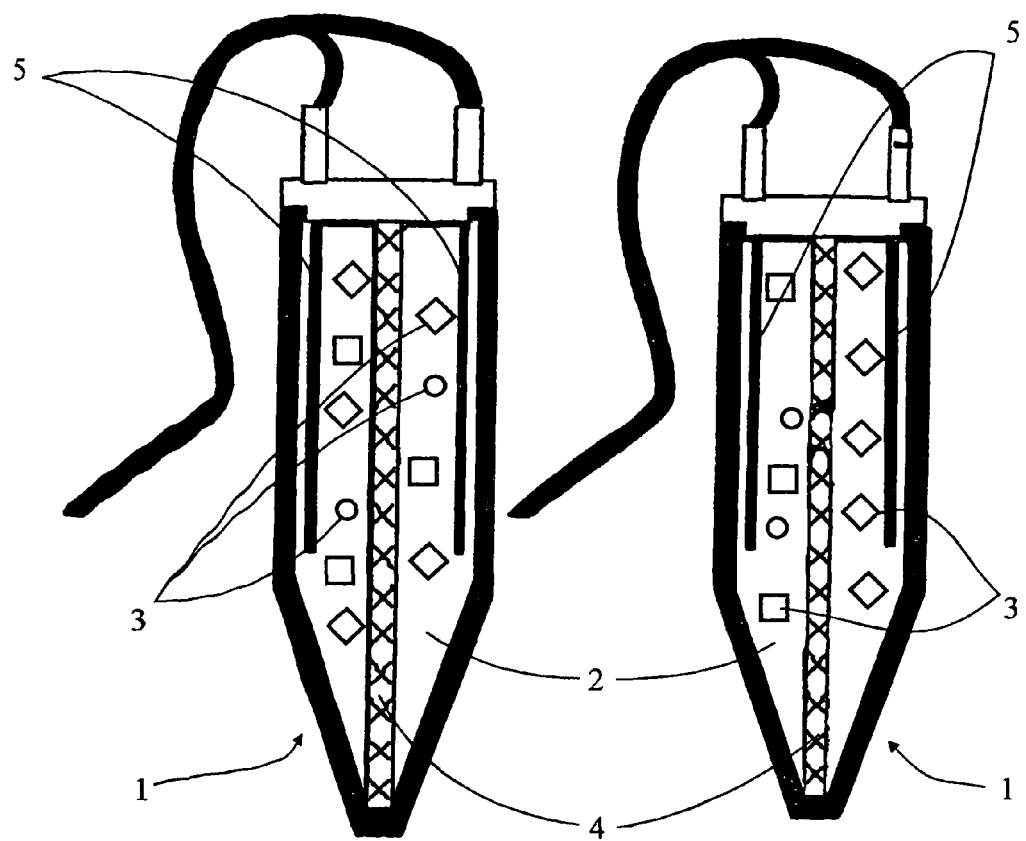
FIGS. 1A and 1B are cross-sections of a filtration reservoir on the filtration device of the invention, said filtration reservoir containing the molecules in solution which have and have not been subjected to the action of an electrical field, respectively.

For purposes of simplicity, the remainder of the description will use only the term filtration to denote filtration and/or separation.

BEST WAY TO ACHIEVE THE INVENTION AND POSSIBLE INDUSTRIAL APPLICATIONS

With reference to FIGS. 1A and 1B, filtration reservoirs 1 are used to filter molecules, in the form of test tubes, measurement beakers, or flasks, for example, into which a solution 2 is injected containing molecules 3 to be filtered. The generic term solution denotes a liquid, a gel, a liquid gel, or other equivalent. Each filtration reservoir 1 comprises a filtration means 4 such as, for example, a filter located generally in the median plane of filtration reservoir 1 and separating it into two chambers. The filtration means 4 allows only the selective passage of molecules 3 according to a predetermined physical or chemical parameter.

The molecules are next subjected to an electrical field by an electrical field generating means such as, for example, electrodes 5 which tend to provoke displacement of the molecules from one chamber to the other. These electrodes 5 may be made of platinum, iridium dioxide, metal, or any type of electrically conductive alloy and inserted into ceramic or some other equivalent material or electrically insulating material. Depending upon the filter 4 used, certain molecules 3 can pass through it, while others are blocked. Molecules 3 are therefore filtered according to the filtration parameters predetermined by the choice of filter 4. These parameters may be, for example, the size, the pI, or the charge of molecules 3. For example, one of the following filters 4 would be used:

a cut-off filter or selective porosity filter, filtering molecules according to their size;

an isoelectric filter, filtering the molecules according to their isoelectric point pI;

an electrophoretic filter or an ion exchange filter, filtering the molecules according to their electrical charge.

The filtration process proceeds as follows:

when electrodes 5 are not charged, there is no electrical field (cf. FIG. 1A). Molecules 3 are randomly distributed in the two filtration reservoir chambers 1 if solution 2 has been injected into each side of filter 4, or in a single chamber if the solution has been injected into a single side of filter 4, the other chamber being filled with a buffer solution; and when electrodes 5 are charged, they generate an electrical field (cf. FIG. 1B) provoking displacement of molecules 3. Then, depending upon their characteristics and those of the filter 4 selected, molecules 3 may or may not pass through filter 4. This results in two chambers containing molecules 3 in solution 2 differentiated according to the predetermined filtration parameters. The filtered molecules 3 from one or both chambers can then be recovered by removing them to again be filtered according to other criteria, or to be used in a specific application.

As will be seen from the rest of the description, the filtration device and method of the invention make it easy to combine different filtration techniques with multiple filtration criteria while allowing very flexible, upgradeable sequential filtration.

For the isoelectric filtration technique, which is used here for sorting proteins, an isoelectric filter 4 is used which divides filtration reservoir 1 into two chambers of different pH levels. This filter 4 consists of an isoelectric membrane capable of exchanging and electrically conducting ions of different polarities in opposite directions. These isoelectric membranes 4 may be made according to the general method described in the publication "Advances in Electrophoresis—Volume 5" authored by Faupel, Righetti and Wenisch, published in 1992, edited by A. Chrambach, M. J. Dunn, B. J. Radola, VCH, Weinheim, N.Y., Basel, Cambridge, ISSN 0932-3031 and reprinted by the Amersham Society in the publication "Protocol Guide de l'isoprime" [Isoprime Protocol Guide] (Article 80-6350-18) in 1997. These isoelectric membranes 4 can be purchased from specialized companies or created according to need. They are capable of modulating the charge of the macro-ions with the help of a continuous titration mechanism. In addition, they have good pI buffering power and pores large enough to admit molecules such as proteins, high mechanical resistance, and good chemical stability allowing them to cover pH ranging from 3 to 11, despite being in the presence of additives such as oxidant agents and chemical or biochemical aggressors.

Molecules 3 for filtration are electrically charged, allowing them to migrate in an electrical field. In the presence of the electrical field, the displacement of charged molecules 3 becomes selective and takes place in different milieus, one formed by the solution 2 (liquid phase), the other formed by the isoelectric membrane 4 (solid or gel phase). Because of its elevated buffering capability, isoelectric membrane 4 conserves a fixed pH. Conversely, the pH prevailing on each side of isoelectric membrane 4 evolves overtime and during the displacement of molecules 3. This pH evolution is considerable when the filtration of molecules 3 begins and then diminishes progressively.

Because of isoelectric membrane 4, molecules 3 are not at their pI, but at a slightly higher or lower pH. For this reason, molecules 3 such as the proteins do not precipitate. The displacement speed of molecules 3 is proportionate to their charge, which is itself proportionate to the difference between the pH of the milieu and the pI of molecule 3. Molecules 3 are displaced in the electrical field in proportion to the difference between the pH and the pI. When the pH is equal to the pI, molecules 3 possess no net charge, as the number of positive charges is equal to that of the negative charges, and molecules 3 no longer become displaced. A stage of equilibrium is thus attained.

The displacement speed of molecules 3 depends on factors such as:

the nature of solution 2, particularly its dielectric constant, viscosity, ionic force, and pH;

the nature of molecule 3, particularly its global electric charge, shape, size, and concentration;

the temperature acting directly on the viscosity of solution 2, the dielectric constant, pH, and stability of molecule 3.

It is apparent that any principle for filtering molecules 3 that is complementary to isoelectric filtration may be used with device 10 and the filtration method of the invention.

According to the invention and with reference to FIGS. 2A through 3D, filtration device 10 comprises three molecule filtration zones 11a-11c, each equipped with a unit of independent filtration reservoirs 1 for filtering molecules 3 in solution 2. Filtration reservoirs 1 are supported and grouped by series in openings 120 provided on supports 12a-12c located on a common chassis 13. Filtration device 10 also comprises a mechanized tool holder 20 holding one or more tools 5, 30-33, said tool holder 20 being coupled with a displacement means 50 and a computerized control means, not shown, directing the displacement of tool holder 20 and/or the operation of tools 5, 30-33.

Filtration device 10 also optionally comprises a preparation zone 11d equipped with one or more containers 40, 41, such as, for example, a container for filtered molecules 3, a buffer container, a waste container, a solvent container, a cleaning container, an additive container, a chemical and/or biological reaction container, or any other appropriate container.

In the examples provided, the displacement means 50 comprises two generally parallel rails 51 formed of upright pieces located on either side of filtration zones 11a-11c, and to which carriage 52 is attached so as to move in translation along axis Y. Said carriage 52 defines a slide to which tool holder 20 is attached so as to move in translation along axis X. Displacement means 50 comprises movement transmitting mechanisms (not shown) such as, for example, a belt-pulley, chain and pinion, endless screw, gears, rack and pinion, or other suitable mechanism driven by an actuator such as, for example, a cylinder, a motor, a reduction gear motor, or some other suitable actuator. Displacement means 50 is controlled by a computerized control means (not shown) allowing displacement of tool holder 20 relative to carriage 52 and of carriage 52 relative to rails 51. Tool holder 20 can thus be displaced in a generally parallel plane relative to filtration zones 11a-11c and preparation zone 11d in order to position tool 5, 30-33 in some location above these filtration zones 11a-c and/or preparation zone 11d. Tool holder 20 can also be attached so as to move in translation along axis Z relative to chariot 52 in order to displace tool 5, 30-33 vertically relative to filtration zones 11a-11c and preparation zone 11d. It can also be pivotably attached. This allows tool 5, 30-33 to be precisely positioned along three axes. The computerized control means comprises, for example, a central unit (not shown) controlled by a computer running one or more software programs.

According to a variation that is not shown, carriage 52 and upright pieces 51 may be replaced by an overhead support movable in translation on rails integral with chassis 13.

Generally speaking, tool holder 20 may hold one or more tools 5, 30-33 chosen according to the operations to be performed, some examples of which are described below. First, tool holder 20 holds one or more pairs of electrodes 5 supplied with electricity in order to effect at least the isoelectric filtration of the molecules in one or more reservoirs simultaneously and automatically. Next, tool holder 20 holds gripping tools 30 such as, for example, a claw, jaws, an electromagnetic grip, a syringe holder, gripping fingers, etc., for holding, displacing, and depositing one or more filtration reservoirs 1, other electrodes 5 independent of tool holder 20, syringes 31, filters 4, or any other appropriate element. Tool holder 20 may also hold removal and/or injection tools 31, such as, for example, a syringe, a piston, etc., for injecting and drawing off a solution, an additive, molecules 3 in solution 2, filtered molecules, etc. Tool holder 20 comprises a means for positioning tools 5, 30-33 on from one to three axes: in rotation, translation, and/or any combination of movements. Tools 5, 30-33 may be stored in a tool compartment (not shown) to which tool holder 20 moves and selects the tool or tools either in succession or simultaneously. Tool holder 20 can also carry several tools 50, 30-33 simultaneously.

Different steps in the filtration procedure using filtration device 10 are described below. It is apparent that other steps which are not described are possible. In these examples, the three filtration zones 11a-11c in filtration device 10 are partially equipped with filtration reservoirs 1, with a portion of openings 120 located in supports 12a-c being unused. Only a portion of filtration reservoirs 1 that are present contain molecules 3 to be filtered, already filtered, or undergoing filtration.

FIGS. 2A and 3A show filtration device 10 during the step of gripping a filtration reservoir 1. For this step, tool holder 20 comprises a gripping claw 30 allowing an individual filtration reservoir 1 to be gripped in order to displace it in a horizontal plane relative to filtration zone 11a-11c and to rails 51. Gripping claw 30 may be pivoting and/or inclinable to pivot and/or incline filtration reservoir 1 as needed. The unit of tool holders 20 may also be pivoting and/or inclinable relative to carriage 52. Three of filtration reservoirs 1 in filtration zone 11b are equipped with electrodes 5 independent of tool holder 20, allowing activation of the electrical field necessary for filtration of molecules 3. In this case, electrodes 5 may be removable or attached to filtration reservoirs 1. They may comprise connecting terminals (not shown) for selective connection. Thus, it is possible to simultaneously effect the operations of filtration in certain filtration reservoirs 1 and displacement of other filtration reservoirs 1 and/or containers 40. In this example, preparation zone 11d comprises six containers 40 for receiving filtered molecules 3. Obviously, tool holder 20 may receive any other type of suitable gripping tools 30.

FIGS. 2B and 3B show filtration device 10 during the step of injecting and/or drawing off molecules 3 in solution 2. For this step tool holder 20 comprises a syringe 31 used to inject molecules 3 in solution 2, another solution, an additive, and/or remove a portion of molecules 3 in solution 2 after filtration. In this example, syringe 31 is integral with tool holder 20. It is of course possible for syringe 31 to be external, held by a gripping tool 31 as previously described or any other suitable tool. Said syringe 31 may be replaced by a piston or any other similar removal and/or injecting means. Syringe 31 may be displaced from one filtration reservoir 1 to another and/or toward containers 41. Syringe 31 may be either fixed or movable in relation to tool holder 20. During this step, preparation zone 11d is provided with four containers 41 larger in size than the preceding ones and used, as needed, as receptacles for filtered molecules, buffer receptacles, waste receptacles, solvent and/or cleaning receptacles. In FIGS. 2B, 3B only one of filtration reservoirs 1 in filtration zone 11b is equipped with electrodes 5 independent of tool holder 20 in order to activate the electrical field.

FIG. 2C represents filtration device 10 during the step of positioning a pair of electrodes 5 associated with tool holder 20 in a filtration reservoir 1 in order to effect the filtration operation directly and automatically with tool holder 20. During this step, the supply of electricity to electrodes 5 is furnished through tool holder 20, which may have an electromagnetic sleeve 32 for holding the pair of magnetized electrodes 5. It is apparent that the pair of electrodes 5 may be gripped by any other appropriate tool such as, for example, a claw, jaws, a suction or vacuum device, etc.

In FIGS. 2D, 3C and 3D, tool holder 20 supports a gripping arm 33 equipped with eight electromagnetic sleeves 32 allowing up to eight pairs of electrodes 5 to be simultaneously transported in columns generally parallel to rails 51 and/or lines generally parallel to carriage 52 and/or on the diagonal for the purpose of performing the filtration operation directly and automatically in eight filtration reservoirs 1 simultaneously. This gripping arm 33 is attached rotatably on tool holder 20 so it can be pivoted as shown in the example of FIGS. 3C and 3D.

Generally speaking, filtration device 10 may comprise several removable and interchangeable tool holders 20 that can be added or substituted in order to perform a broad range of functions.

According to a variation that is not shown, each filtration zone 11a-11c may be provided on a support 12a-12c independent of the others. These supports 12a-12c may be coupled with a displacement means (not shown) guided by the control means to move in translation along three axes and/or in rotation, said displacements being vertical and/or horizontal. These supports 12a-12c or any other portion of filtration device 10 may be equipped with an air conditioning means (not shown) for regulating the temperature of the contents of filtration reservoirs 1, for example, to prevent evaporation of the buffer solutions they contain, regulate filtration speed, or maintain a solution 2 at a predetermined temperature. Filtration device 10 may also be sealed in an isothermal enclosure.

According to another embodiment of filtration device 10 not shown, the displacement means 50 comprises one or more articulated mechanical arms controlled by the computerized control means, said one or more articulated mechanical arms being designed to carry the tool holder or tool holders 20. The base of these articulated mechanical arms may be either fixed or movable relative to chassis 13. These articulated mechanical arms may be removable and interchangeable, with each articulated mechanical arm capable of holding one or more removable interchangeable tool holders 20 so that tool 5, 30-33 can be adapted according to need.

The computerized control unit is governed by a computerized central processor run by one or more computer or software programs, allowing the filtration operations to be completely automated by controlling tool holder 20 and/or tools 5, 30-33 and/or filtration supports 12a-12c. This makes it possible to displace, inject, filter, or draw off molecules 3 in solution, solutions, additives and the like, as required. Thus, the filtration of molecules 3 may be refined according to several predetermined criteria through the successive performance of several operational sequences; these sequences may be limitless and conducted in parallel. The computerized control allows multiple filtration sequences, either repetitive or non-repetitive, to be elaborated and performed automatically. Obviously, the control means can be programmed to adapt the filtration sequences on a case-by-case basis to fulfill specific requirements, depending upon the desired results and the molecules to be filtered.

The filtration method and device 10 of the invention offer a means for simply, quickly, and effectively combining several filtration or other operations, consecutively and/or simultaneously. Thus, it is possible to perform the following steps:

Injection of molecules 3 in solution 2 to be fractionated in a first filtration reservoir 1;

Performing a first filtration using isoelectric focalization;

Removal of at least a portion of the filtered molecules 3;

Introduction of this sample into a second filtration reservoir 1;

Performing a second filtration using isoelectric focalization;

Removal of at least a portion of the filtered molecules 3;

Introduction of this sample into a third filtration reservoir 1;

Performing a third filtration using selective porosity (Cut-Off);

Removal of at least a portion of the filtered molecules 3.

Any other combination of compatible or complementary operations is, of course, possible, including placing molecules 3 in an enzyme bath or in a solution 2 containing affinity supports, specific ligands, or even in a solution 2 containing magnetized supports.

This description clearly demonstrates that the filtration method and device 10 of the invention respond to the objectives stated, and particularly that one of their principal advantages over prior art filtration methods and devices is improved filtration time. This filtration device 10 actually makes it possible for several operations to take place simultaneously. In addition, less time is required due to the presence of a single filter 4 in each filtration reservoir 1. Molecules 3 have only a single filter 4 to pass through per operation, significantly reducing filtration time in comparison to methods which rely on a cascade of filters. Filtration time is reduced further by the very small distance separating electrodes 5.

Another important advantage is the flexibility of filtration operations possible and the variety of these operations. In addition, automated control optimizes performance without adversely affecting the quality of each manipulation, resulting in improved precision and reliability.

Finally, as to the objectives of tracking and analyzing results, the parameters of each filtration are easily recorded by the computer. Obviously, these results can be transmitted by any appropriate means of communication.

The present invention is not limited to the exemplary embodiments described, but extends to any modification and variation obvious to a person skilled in the art while still remaining within the scope of protection defined by the attached claims.

The invention claimed is:

1. A filtration device (10) for at least one of filtration and separation of molecules (3) and proteins, the device comprising at least one filtration zone (11a-11c) comprising a plurality of independent filtration reservoirs (1) capable of receiving a solution containing the molecules (3), the filtration reservoirs (1) being equipped with a filtration means (4) for filtering the molecules (3) according to at least one of a predetermined physical parameter and a chemical parameter, and a means for generating at least one electrical field (5) to cause displacement of at least a portion of the molecules (3) through the filtration means (4), the filtration reservoirs (1) being one of a test tube, a flask, a measurement beaker, and the filtration means (4) comprises a filter located generally along an axis of symmetry of the filtration reservoirs (1) separating the filtration reservoirs (1) into two chambers, the filter separating the molecules according to at least one of the predetermined physical parameter and chemical parameter, the filtration device (10) also comprising at least one mechanized tool holder (20) provided with at least one tool (5, 30-33), the tool holder (20) being equipped with at least one pair of electrodes (5) supplied with electricity to form the electrical field generation means and directly and automatically performing the filtration operation in the filtration reservoirs (1), the tool holder (20) being coupled with a displacement means (50) for displacing at least the tool relative to the filtration zone for placing the electrodes (5) in at least one filtration reservoir (1), before filtration, and removing the electrodes (5), after filtration, the tool holder (20) also being coupled with computerized control means for controlling displacement and the operation of the tool carried thereby.

2. The filtration device (10) according to claim 1, wherein the filter is one of an isoelectric filter, a selective porosity filter, and an ion exchange filter, the filter separating the molecules according to at least one of an isoelectric point (pI), a size, and an electrical charge.

3. The filtration device (10) according to claim 1, wherein the tool holder (20) is provided with several pairs of electrodes (5) and the tool holder (20) directly and automatically performs an isoelectric filtration operation simultaneously in a plurality of filter reservoirs (1).

4. The filtration device (10) according to claim 1, wherein the displacement means comprises at least one carriage (52) holding the tool holder (20), the carriage (52) being movable on a chassis (13) in order to displace the tool (5, 30-33) relative to the filtration zone (11a-11c).

5. The filtration device (10) according to claim 4, wherein the displacement means comprises two rails (51) generally extending parallel to one another for guiding the carriage (52) in translation generally parallel to the filtration zone (11a-11c).

6. The filtration device (10) according to claim 5, wherein the rails (51) are supported by upright portions integral with the chassis (13) and located on either side of the filtration zone (11a-c).

7. The filtration device (10) according to claim 5, wherein the rails (51) are integral with the chassis (13) and the carriage (52) defines an overhead support element.

8. The filtration device (10) according to claim 4, wherein the carriage (52) comprises a slide to which the tool holder (20) is attached so as to move in translation.

9. The filtration device (10) according to claim 4, wherein the filtration device (10) comprises at least one of several of the carriages (52), articulated arms and the tool holders (20) designed to be removable and interchangeable.

10. The filtration device (10) according to claim 9, wherein the one or more mechanized tool holder comprises at least one tool holder (20) dedicated to the filtration operation and at least one other tool holder (20) dedicated to at least one complementary operation, and the at least one complimentary operation being selected from the group consisting of manipulating filtration reservoirs (1), manipulating electrodes (5), one of removing and injecting a solution, an additive, molecules in solution, filtered molecules.

11. The device (10) according to claim 10, wherein the tool holder (20) comprises at least one complementary tool (30-33), the complimentary tool being one of a claw (30), an electromagnetic gripping device (32), a syringe holder, gripping fingers, gripping arm (33), gripping jaws, a syringe (31), a piston, a suction device, and a vacuum system.

12. The filtration device (10) according to claim 1, wherein the displacement means comprises at least one articulated arm holding said tool holder (20), the displacement means communicating with the tool holder (20) such that the electrodes (5) of the tool holder (20) are displacable from one filter reservoir (1) to at least one other filter reservoir (1).

13. The filtration device (10) according to claim 1, wherein the filtration reservoirs (1) are held by at least one support (12a-12c) coupled with a complementary displacement means driven by the control means which displaces the support (12a-c) in at least one of translation and rotation relative to at least one of the filtration zone (11a-c) and the tool holder (20).

14. The filtration device (10) according to claim 1, wherein the filtration device (10) comprises at least one preparation zone (11d) allowing at least one of pre- and post-filtration operations, the pre- and the post-filtration operations being storing molecules, rinsing, diluting, disinfecting, introducing additive, waste.

15. The filtration device (10) according to claim 14, wherein the preparation zone (11d) is equipped with at least one container (40, 41) selected from the group consisting of a molecule storage container, a buffer container, a waste container, a solvent container, a cleaning container, a chemical and a biological reaction container.

16. The filtration device (10) according to claim 1, wherein a computerized control means is driven by at least one central unit run by at least one software program for controlling the filtration device.

17. The filtration device (10) according to claim 1, wherein the displacement means comprises at least one of the actuators selected from the group comprising a motor, a reduction gear motor, a cylinder, and an electromagnet.

18. The filtration device (10) according to claim 1, wherein the filtration zone (11a-c) is coupled with an air conditioning means for regulating at least the temperature of said filtration reservoirs (1).

19. The filtration device (10) according to claim 18, wherein the air conditioning means comprises at least one thermally regulated enclosure capable of receiving the filtration device (10).

20. A filtration device (10) for at least one of filtration and separation of molecules (3) and proteins, the device comprising:
    at least one filtration zone (11a-11c) comprising a plurality of independent filtration reservoirs (1) capable of receiving a solution containing the molecules (3), each of the filtration reservoirs (1) being equipped with a filtration means (4) for filtering the molecules (3) according to at least one of a physical parameter and a chemical parameter;
    a means for generating at least one electrical field (5) to cause displacement of at least a portion of the molecules (3) through the filtration means (4);
    the filtration reservoirs (1) being one of a test tube, a flask, a measurement beaker;
    the filtration means (4) comprising a filter located generally along an axis of symmetry of the filtration reservoirs (1) and separating the filtration reservoirs (1) into two chambers, the filter separating the molecules according to at least one of the physical parameter and the chemical parameter;
    the filtration device (10) also comprising at least one mechanized tool holder (20) provided with at least one tool (5, 30-33), the tool holder (20) being equipped with at least one pair of electrodes (5) supplied with electricity to form the electrical field generation means for directly and automatically performing the filtration operation of the filtration reservoirs (1), the tool holder (20) being coupled with a displacement means (50) for displacing at least the tool relative to the filtration zone for placing the electrodes (5) in at least one filtration reservoir (1), prior to filtration, and removing the electrodes (5), following filtration;
    the tool holder (20) also being coupled with computerized control means for controlling displacement and the operation of the tool being carried by the tool holder (20); and
    each of the pair of electrodes being displaceable into a respective one of the two chambers on opposing sides of the filter.

* * * * *